(12) United States Patent
Nisi et al.

(10) Patent No.: US 11,672,628 B2
(45) Date of Patent: Jun. 13, 2023

(54) MODULAR MOUTHPIECE

(71) Applicant: Indiana University Research and Technology Corporation, Indianapolis, IN (US)

(72) Inventors: Timothy L. Nisi, Carmel, IN (US); Brian D. Overshiner, McCordsville, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 77 days.

(21) Appl. No.: 17/017,115

(22) Filed: Sep. 10, 2020

(65) Prior Publication Data

US 2021/0068922 A1 Mar. 11, 2021

Related U.S. Application Data

(60) Provisional application No. 62/898,637, filed on Sep. 11, 2019.

(51) Int. Cl.
*A61C 5/90* (2017.01)

(52) U.S. Cl.
CPC ...................... *A61C 5/90* (2017.02)

(58) Field of Classification Search
CPC . A61C 5/90; A61C 9/0006; A61C 19/06–066; A63B 23/032; A61F 5/56; A61F 5/566; A61F 5/58; A61F 2005/563; A61N 5/1014; A61N 5/90; A61N 5/1001

USPC ......................................................... 433/140
See application file for complete search history.

(56) References Cited

U.S. PATENT DOCUMENTS

| | | | |
|---|---|---|---|
| 8,430,102 B2 | 4/2013 | Westbrook et al. | |
| 8,496,008 B2 | 7/2013 | Westbrook et al. | |
| 9,414,896 B2 | 8/2016 | Giffey et al. | |
| 9,504,537 B2 * | 11/2016 | Johnson | A61N 5/10 |
| 9,937,019 B1 * | 4/2018 | Copps | A61C 19/06 |
| 2007/0068535 A1 | 3/2007 | Colman et al. | |

FOREIGN PATENT DOCUMENTS

WO WO-2017192676 A1 * 11/2017 ............. A61B 13/00

OTHER PUBLICATIONS

B. Johnson et al., Fabrication of customized tongue-displacing stents: considerations for use in patients receiving head and neck radiotherapy, JADA 2013;144(6):594-600.
Klarity BiteLok instructions for use.

* cited by examiner

*Primary Examiner* — Nicholas D Lucchesi
(74) *Attorney, Agent, or Firm* — Barnes & Thornburg LLP (57) ABSTRACT

A modular mouthpiece for soft tissue placement includes a base tray and soft tissue placement inserts. The soft tissue placement inserts are configured to be selectively coupled to the base tray.

20 Claims, 5 Drawing Sheets

MODULAR MOUTHPIECE

CROSS REFERENCE TO RELATED APPLICATIONS

This application claims priority to and the benefit of U.S. Provisional Patent Application No. 62/898,637, filed 11 Sep. 2019, the disclosure of which is now expressly incorporated herein by reference.

FIELD OF THE DISCLOSURE

The present disclosure relates generally to oral medical treatment devices, and more specifically to devices for positioning soft tissue during oral medical treatments.

BACKGROUND

Oral medical treatments sometimes require specific placement of soft tissue to access locations of interest. Foam blocks, cotton balls, and the like have been used to place soft tissues during such treatments. These solutions can be unstable and/or not repeatable, leading to the need for other devices to address this need.

SUMMARY

A modular mouthpiece adapted for soft tissue location during oral therapies may include a base tray and a plurality of soft tissue inserts. The base tray is arranged between upper and lower teeth of a patient. The plurality of soft tissue placement inserts are configured to be selectively coupled to the base tray to allow a patient to customize the modular mouthpiece for optimal fit and comfort.

The base tray and the soft tissue placement inserts may come in a range of sizes, such as small, medium, and large, so that the patient may select the appropriate size for a correct and comfortable fit within a mouth of the patient. The different sizes of the base tray and soft tissue placement inserts may help accurately position the soft tissue of the patient in such a way that may help the treatment reach the intended target and avoid the healthy tissue.

The base tray and soft tissue placement inserts may also be helpful repeatedly and accurately positioning the soft tissue of the patient during multi-session oral therapies. This is especially important during radiation therapy. Accurate, repeatable positioning of the mandible and tongue throughout the radiation treatment is important for achieving the maximum possible dose of radiation to reach the intended target areas while bypassing healthy bone and tissue.

These and other features of the present disclosure will become more apparent from the following description of the illustrative embodiments.

DETAILED DESCRIPTION OF THE DRAWINGS

For the purposes of promoting an understanding of the principles of the disclosure, reference will now be made to a number of illustrative embodiments illustrated in the drawings and specific language will be used to describe the same.

Figure 1:
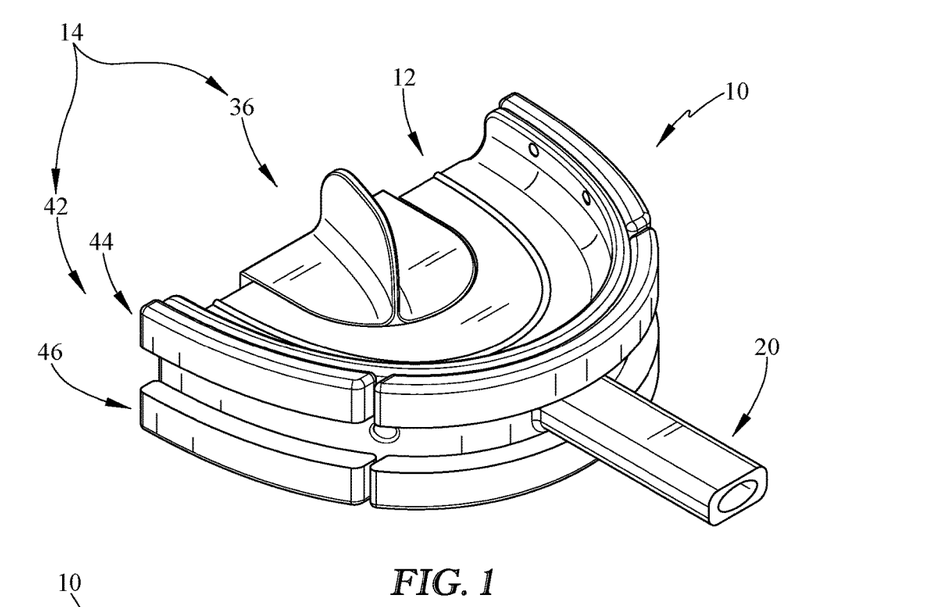
FIG. 1 is a perspective view of a modular mouthpiece for soft tissue location during oral therapies.

A modular mouthpiece 10 adapted for soft tissue location during oral therapies is shown in FIG. 1. The modular mouthpiece 10 includes a base tray 12 and a plurality of soft tissue inserts 14 as shown in FIGS. 1-4. The plurality of soft tissue placement inserts 14 are configured to be selectively coupled to the base tray 12 to allow a patient to customize the modular mouthpiece 10 for optimal fit and comfort.

The base tray 12 and the soft tissue placement inserts 14 may come in a range of sizes, such as small, medium, and large, so that the patient may select the appropriate size for a correct and comfortable fit within a mouth of the patient. The different sizes of the base tray 12 and soft tissue placement inserts 14 help accurately position the soft tissue of the patient in such a way that may help the treatment reach the intended target and avoid the healthy tissue.

The base tray 12 and soft tissue placement inserts 14 may also be helpful repeatedly and accurately positioning the soft tissue of the patient during multi-session oral therapies. This is especially important during radiation therapy. Accurate, repeatable positioning of the mandible and tongue throughout the radiation treatment is important for achieving the maximum possible dose of radiation to reach the intended target areas while bypassing healthy bone and tissue.

The base tray 12 includes a U-shaped bite plate 16 and a lip positioner support 18 as shown in FIGS. 1-4. The U-shaped bit plate 16 is configured to be arranged between upper and lower teeth of the patient. The lip positioner support 18 extends from an outer edge 28 of the U-shaped bite plate 16.

The lip positioner support 18 includes an upper portion 32 and a bottom portion 34 as shown in FIGS. 1-4. The upper portion 32 extends upwardly from the outer edge 28 of the bite plate 16 around the upper teeth of the patient. The bottom portion 34 extends downwardly from the outer edge 28 of the bite plate 16 around the bottom teeth of the patient.

The soft tissue placement inserts 14 include a tongue guide insert 36 and at least one lip placement insert 42 as shown in FIGS. 1-4. The tongue guide insert 36 is selectively coupled to the bite plate 16 of the base tray 12. The tongue guide insert 36 is configured to engage a tongue of the patient to position the tongue in a desired orientation within the mouth of the patient. The lip positioner insert 42 is selectively coupled to the lip positioner support 18 of the base tray 12. The lip positioner insert 42 is configured to engage a lip and gums of the patient to separate the soft tissue of the lip and gums of the patient.

Figure 2:
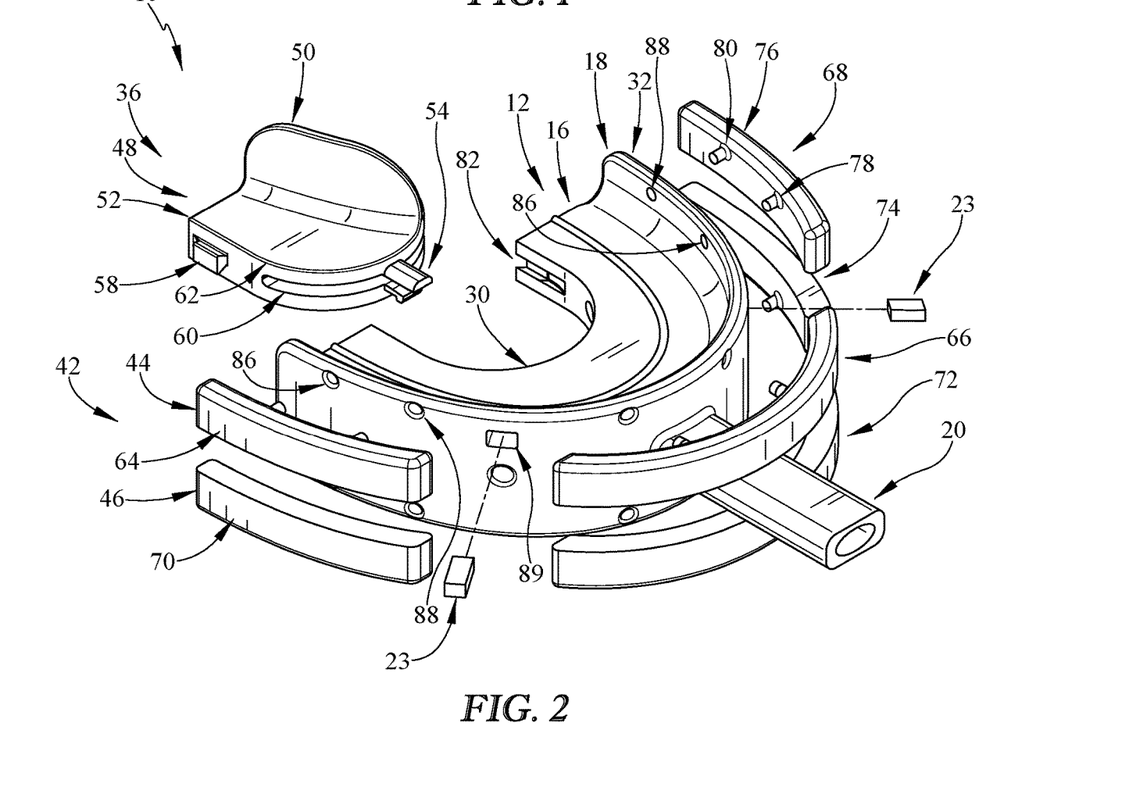
FIG. 2 is an exploded frontal perspective view of the modular mouthpiece of FIG. 1.
Figure 3:
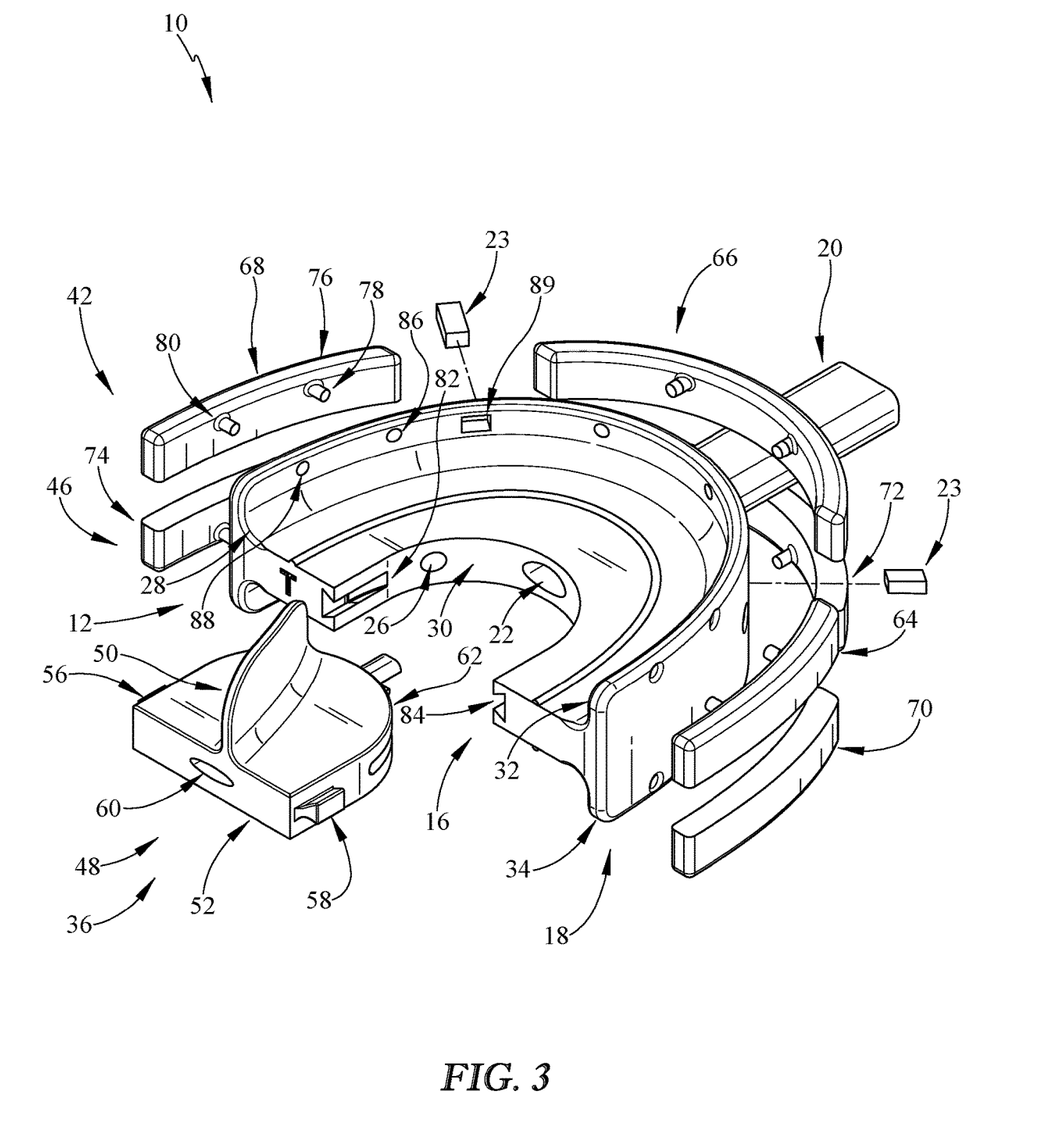
FIG. 3 is an exploded rear perspective view of the modular mouthpiece of FIG. 1
Figure 4:
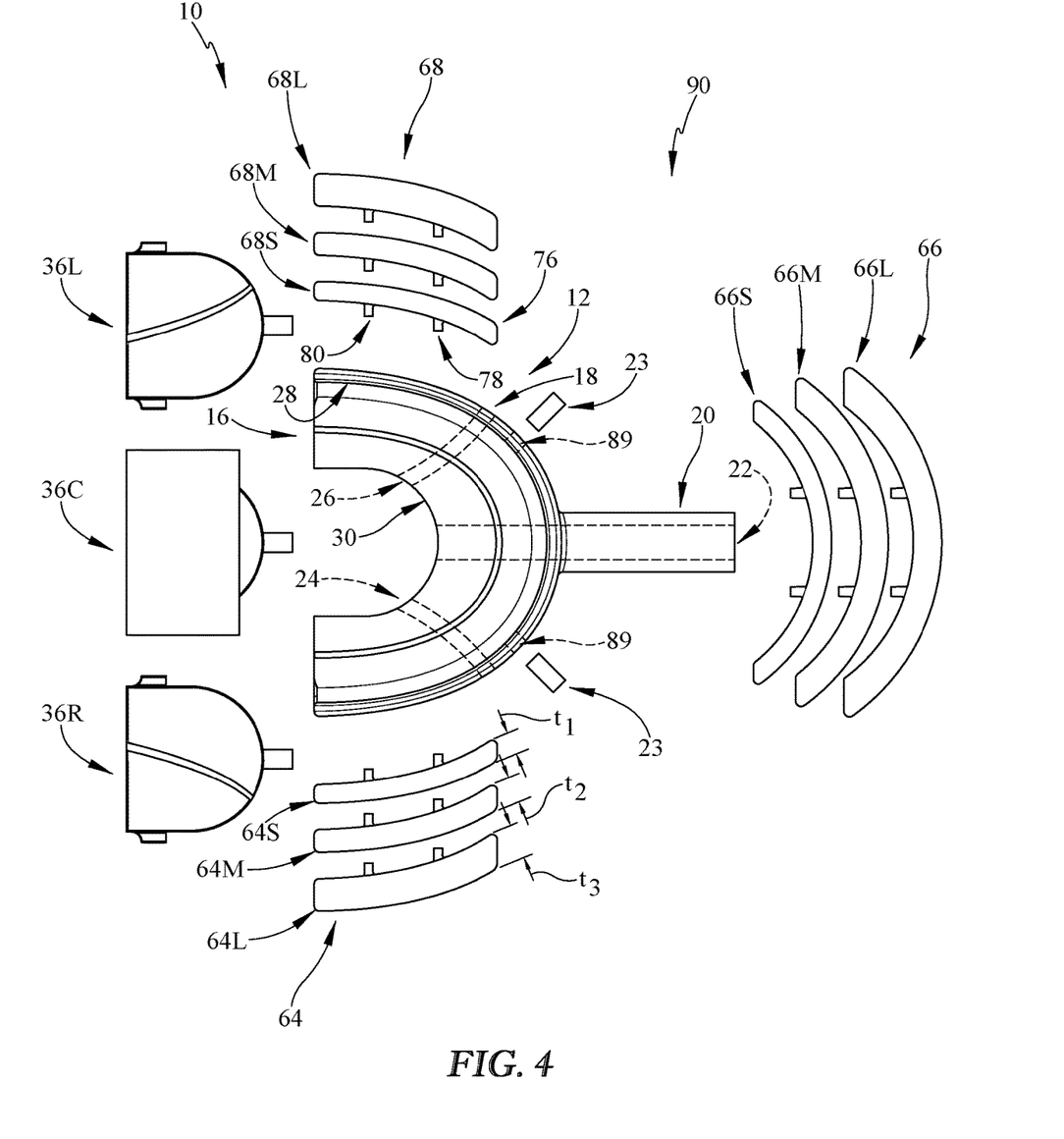
FIG. 4 is a top view of showing the modular mouthpiece includes a base tray and a plurality of soft tissue placement inserts to form a modular mouthpiece kit.

In the illustrative embodiments, the soft tissue placement inserts 14 include a plurality of upper lip positioner inserts 44 and a plurality of bottom lip positioner inserts 46 as shown in FIGS. 2-4. Each of the upper lip positioner inserts 44 is selectively coupled to the upper portion 32 of the lip positioner support 18, while each of the bottom lip positioner inserts 46 is selectively coupled to the bottom portion 34 of the lip positioner support 18. The upper lip positioner inserts 44 are configured to engage an upper lip and gums of the patient. The bottom lip positioner inserts 46 are configured to engage a bottom lip and gums of the patient.

The tongue guide insert 36 includes a tongue guide base 48 and a tongue guide flange 50 as shown in FIGS. 2-5. The tongue guide base 48 is configured to be selectively coupled to an inner edge 30 of the bite plate 16 of the base tray 12. The tongue guide flange 50 extends upwardly from the tongue guide base 48 and engages the tongue of the patient. The tongue guide flange 50 engages the tongue of the patient to position the tongue toward one of a right side of the mouth, a front center of the mouth, and a left side of the mouth of the patient.

The tongue guide base 48 is shaped to include base plate 52, a plurality of attachment tabs 54, 56, 58, and a channel 60 as shown in FIGS. 3-7. The base plate 52 is shaped to include an outer edge 62 that mates with the inner edge 30 of the bite plate 16 of the base tray 12. The attachment tabs 54, 56, 58 extend from the outer edge 62 of the base plate 52 and engage attachment channels formed in the bite plate 16 of the base tray 12 to selectively couple the tongue guide insert 36 to the base tray 12. The channel 60 extends through the base plate 52.

In the illustrative embodiment, the tongue guide base 48 includes at least three attachment tabs 54, 56, 58 as shown in FIGS. 3-7. The attachment tabs 54, 56, 58 include a front attachment tab 54, a first side attachment tab 56, and a second side attachment tab 58. Each of the attachment tabs 54, 56, 58 mate with corresponding features in the bite plate 16. In the illustrative embodiment, the front attachment tab 54 is a snap fit attachment feature 54 that mates with the bite plate 16

The plurality of upper lip positioner inserts 44 includes a right upper lip positioner insert 64, a center upper lip positioner insert 66, and a left upper lip positioner insert 68 as shown in FIGS. 2-4. The right upper positioner insert 64 is selectively coupled to the upper portion 32 of the lip positioner support 18 on a right side of the modular mouthpiece 10. The center upper positioner insert 66 is selectively coupled to the upper portion 32 of the lip positioner support 18 on a front center of the modular mouthpiece 10. The left upper positioner insert 68 is selectively coupled to the upper portion 32 of the lip positioner support 18 on a left side of the modular mouthpiece 10. Each of the upper positioner inserts 44 are configured to engage the upper lip and gums of the patient on the corresponding right, center, or left side of the mouth of the patient.

The plurality of bottom lip positioner inserts 46 includes a right bottom lip positioner insert 70, a center bottom lip positioner insert 72, and a left bottom lip positioner insert 74 as shown in FIGS. 2-4. The right bottom positioner insert 70 is selectively coupled to the bottom portion 34 of the lip positioner support 18 on the right side of the modular mouthpiece 10. The center bottom positioner insert 72 is selectively coupled to the bottom portion 34 of the lip positioner support 18 on the front center of the modular mouthpiece 10. The left bottom positioner insert 74 is selectively coupled to the bottom portion 34 of the lip positioner support 18 on the left side of the modular mouthpiece 10. Each of the bottom positioner inserts 46 are configured to engage the bottom lip and gums of the patient on the corresponding right, center, or left side of the mouth of the patient.

In the illustrative embodiment, the upper and bottom lip positioner inserts 44, 46 each include at least three lip positioner inserts 64, 66, 68, 70, 72, 74. In other embodiment the upper and bottom lip positioner inserts 44, 46 are continuous inserts 44, 46 that extend along the entire outer edge 28 of the base tray 12. In other embodiments the upper and bottom lip positioner inserts 44, 46 may include more or less than three positioner inserts.

Each of the lip positioner inserts 44, 46 include a lip positioner plate 76 and at least two attachment pegs 78, 80 as shown in FIGS. 2-4. The lip positioner plate 76 extends along the outer edge 28 of the bite plate 16 and has a thickness t1, t2, t3. The attachment pegs 78, 80 extend from the lip positioner plate 76 and engage the lip positioner support 18 to selectively couple the lip positioner inserts 44, 46 to the base tray 12. The attachment pegs 78, 80 are spaced apart along the outer edge 28 of the bite plate 16.

Turning again to the base tray 12, the base tray 12 also includes a handgrip 20 and at least one position indicator tab 59 as shown in FIGS. 1-4. The handgrip 20 extends from the bite plate 16 at the front center of the modular mouthpiece 10. The handgrip 20 is configured to provide a handle for positioning the mouthpiece 10 in the desired orientation within the mouth of the patient. The position indicator tab 23 is coupled to the lip positioner support 18 and configured to move relative to the lip positioner support 18 between a retracted position in which the tab 23 does not extend from and is flush with the lip positioner support 18 and an extended position in which the tab 23 extends from the lip positioner support 18. The tab 23 moves from the retracted position to the extended position to indicate when the tongue of the patient has is in the desired orientation relative to the tongue guide flange 50.

In the illustrative embodiment, the base tray 12 includes a plurality of position indicator tabs 23 as shown in FIGS. 2-4. A position indicator tab 23 may be located on the right side of the mouthpiece 10, at the center of the mouthpiece 10, and the left side of the mouthpiece 10. In the illustrative embodiment, the base tray 12 includes two tabs 23, one located on the right side of the mouthpiece 10 and one located on the left side of the mouthpiece 10.

In some embodiments, the position indicator tab 23 may include a color at an end of the tab 23 extending from lip positioner support 18. The color may help distinguish when the tab 23 is in the extended positon versus when the tab 23 is in the retracted position.

The base tray 12 is also shaped to include a plurality of channels 22, 24, 26 as shown in FIGS. 3 and 4. The plurality of channels 22, 24, 26 extend through the base tray 12 and are configured to provide breathing passageways for the patient. The channels 22, 24, 26 may also provide a passageway for suctioning fluids out of the mouth of the patient.

The plurality of channels 22, 24, 26 include a main suction channel 22 and at least two auxiliary airway channels 24, 26 as shown in FIGS. 3 and 4. The main suction channel 22 extends through the bite plate 16 and the handgrip 20. The auxiliary airway channels 24, 26 extend through the bite plate 16 from the inner edge 30 through the lip positioner support 18 to provide breathing passageways for the patient. In the illustrative embodiment, the plurality of channels 22, 24, 26 converge and align with the channel 60 formed in the base plate 52 of the tongue guide insert 36, when the tongue guide insert 36 is coupled to the base tray 12.

The inner edge 30 of the bite plate 16 is shaped to include a plurality of attachment channels 82, 84 as shown in FIGS. 3 and 4. The attachment channels 82, 84 are configured to mate with the attachment tabs 56, 58 of the tongue guide insert 36 to selectively couple the tongue guide insert 36 to the bite plate 16 of the base tray 12. The first side attachment tab 56 engages a first side attachment channel 82 of the bite plate 16. The second side attachment tab 58 engages a second side attachment channel 84 of the bite plate 16. The front attachment tab 54 engages the bite plate 16 in an opening of the main suction channel 22.

The lip positioner support 18 is shaped to include a plurality of peg holes 86, 88 and an indicator tab channel 89 as shown in FIGS. 2-4. The peg holes 86, 88 are configured to mate with the attachment pegs 78, 80 of each lip positioner insert 42, 44 to selectively couple the lip positioner inserts 42, 44 to the base tray 12. The indicator tab channel 89 extends through the lip positioner support 18 and is configured to receive the tab 23 to couple the tab 23 to the lip positioner support 18. The indicator tab channel 89 is sized to allow the tab 23 to move between the extended and retracted positions.

The base tray 12 and plurality of soft tissue inserts 14 cooperate in accordance with the present disclosure to provide a modular mouthpiece kit 90 as suggested in FIG. 4. The modular mouthpiece kit 90 includes a plurality of base trays 12, a plurality of tongue guide inserts 36, and a plurality of lip positioner inserts 42. The plurality of base trays 12 include a small base tray, a medium base tray, and a large base tray. The plurality of tongue guide inserts 36 are configured to be selectively coupled to the U-shaped bite plate 16 of each base tray 12. The plurality of lip positioner inserts 42 are configured to be selectively coupled to the lip positioner support 18 of each base tray 12.

The plurality of tongue guide inserts 36 include a right tongue guide insert 36R, a center tongue guide insert 36C, and a left tongue guide insert 36L as shown in FIGS. 4-7. The left tongue guide insert 36L is configured to urge the tongue of the patient to the left side of the mouth of the patient. The center tongue insert 36L is configured to urge the tongue of the patient to the center of the mouth of the patient. The right tongue guide insert 36R is configured to urge the tongue of the patient to the right side of the mouth of the patient.

Figure 5:
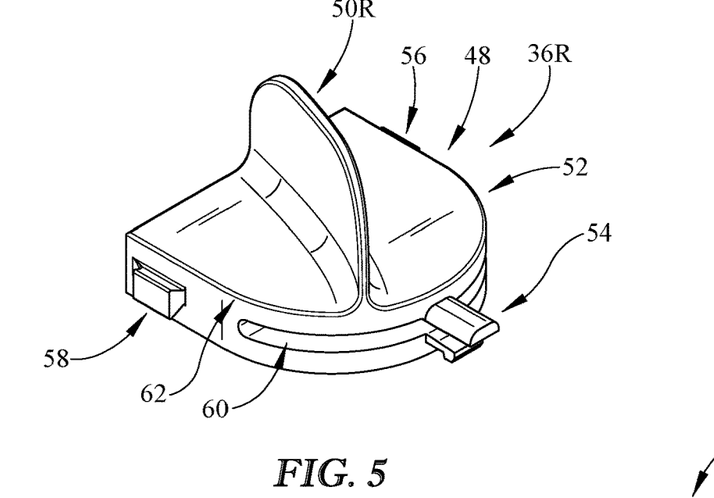
FIG. 5 is a perspective view of a right tongue guide insert included in the plurality of soft tissue placement inserts.

The right tongue guide insert 36R includes a tongue guide base 48 and a right tongue guide flange 50R as shown in FIG. 5. The tongue guide base 48 is selectively coupled to the inner edge 30 of the bite plate 16 of the base tray 12. The right tongue guide flange 50R extends upwardly from the tongue guide base 48 and engages the tongue of the patient. The right tongue guide flange 50R engages the tongue of the patient to position the tongue toward the right side of the mouth of the patient.

Figure 6:
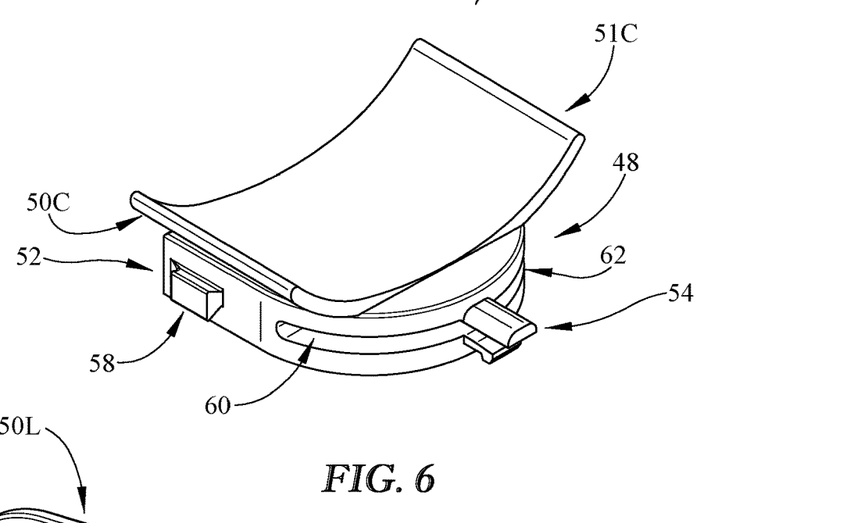
FIG. 6 is a perspective view of a center tongue guide insert included in the plurality of soft tissue placement inserts.

The center tongue guide insert 36C includes a tongue guide base 48 and a center tongue guide flanges 50C, 51C as shown in FIG. 6. The tongue guide flanges 50C, 51C each extend upwardly from the tongue guide base 48 and away from each other to form a U-shape that engages the tongue of the patient. The tongue guide flange 50C, 51C engage the tongue of the patient to position the tongue toward the center of the mouth of the patient.

Figure 7:
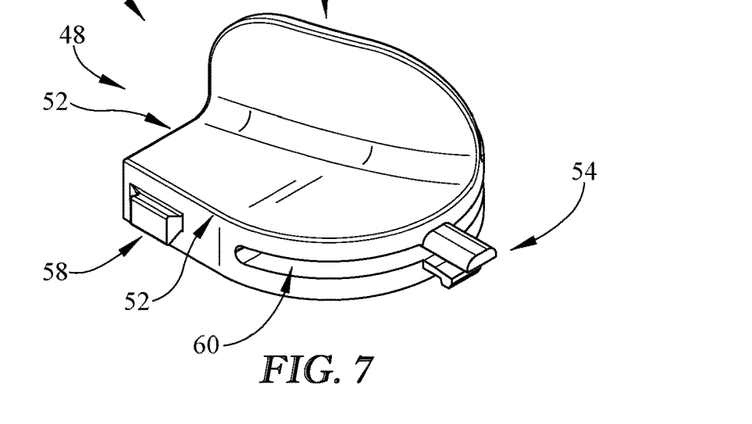
FIG. 7 is a perspective view of a left tongue guide insert included in the plurality of soft tissue placement inserts.

The left tongue guide insert 36L includes a tongue guide base 48 and a left tongue guide flange 50L as shown in FIG. 7. The left tongue guide flange 50L extends upwardly from the tongue guide base 48 and engages the tongue of the patient. The left tongue guide flange 50L engages the tongue of the patient to position the tongue toward the left side of the mouth of the patient.

The plurality of lip positioner inserts 42 include the plurality of upper lip positioner inserts 44 and the plurality of bottom lip positioner inserts 46 as shown in FIGS. 3 and 4. The upper lip positioner inserts 44 are configured to engage the upper lip and gums of the patient to separate the soft tissue of the upper lip and gums of the patient. The plurality of bottom lip positioner inserts 46 are configured to engage the bottom lip and gums of the patient to separate the soft tissue of the bottom lip and gums of the patient.

Each of the plurality of upper and bottom lip positioner inserts 44, 46 include a plurality of right lip positioner inserts 64, 70, a plurality of forward center lip positioner inserts 66, 72, and a plurality of left lip positioner inserts 68, 74, as shown in FIGS. 3 and 4. The right lip positioner inserts 64, 70 engage the lip and gums on the right side of the mouth of the patient, while the left lip positioner inserts 68, 74 engage the lip and gums on the left side of the mouth of the patient. The forward center lip positioner inserts 66, 72 engage the front center of the mouth of the patient.

The plurality of right lip positioner inserts 64 include a small lip positioner insert 64S, a medium lip positioner insert 64M, and a large lip positioner insert 64L. The small lip positioner insert 64S has a first thickness t1, the medium lip positioner insert 64M has a second thickness t2, and the large lip positioner insert 64L has a third thickness t3. The thickness t2 of the medium positioner insert 64M is larger than the thickness t1 of the small lip positioner insert 64S, but smaller than the thickness t3 of the large lip positioner insert 64L.

The plurality of front center lip positioner inserts 66 includes a small lip positioner insert 66S, a medium lip positioner insert 66M, and a large lip positioner insert 66L. The small lip positioner insert 66S has the first thickness t1, the medium lip positioner insert 66M has the second thickness t2, and the large lip positioner insert 66L has the third thickness t3. The thickness t2 of the medium positioner insert 66M is larger than the thickness t1 of the small lip positioner insert 66S, but smaller than the thickness t3 of the large lip positioner insert 66L.

The plurality of left lip positioner inserts 68 includes a small lip positioner insert 68S, a medium lip positioner insert 68M, and a large lip positioner insert 68L. The small lip positioner insert 68S has the first thickness t1, the medium lip positioner insert 68M has the second thickness t2, and the large lip positioner insert 68L has the third thickness t3. The thickness t2 of the medium positioner insert 68M is larger than the thickness t1 of the small lip positioner insert 68S, but smaller than the thickness t3 of the large lip positioner insert 68L.

In the illustrative embodiment, the plurality of right, front center, and left bottom lip positioner inserts 70, 72, 74 also include small, medium, and large sizes. In other embodiments, the modular mouthpiece kit 90 includes a plurality of upper lip positioner insert 44 and a plurality of bottom lip positioner inserts 46 that each extend along the entire outer edge 28 of the bite plate 16. In those embodiments, the upper and bottom lip positioner inserts 44, 46 each include small, medium, and large sizes.

A method may include several steps. The method includes selecting one of the small base tray 12, the medium base tray 12, and the large base tray 12, positioning the selected base tray 12 in the mouth of the patient so that the upper and bottom teeth of the patient are engaged with the bite plate 16, and inspecting the fit of the selected base tray 12 in the mouth of the patient.

The inspecting step includes determining if the selected base tray 12 fits correctly or comfortably in the mouth of the patient. If the selected base tray 12 does not fit correctly or comfortably in the mouth of the patient, meaning the base tray 12 is too large or too small, the method includes selecting a different size base tray 12 and repeating the positioning and inspecting steps until the base tray 12 with the correct fit and comfort is selected for the patient. If the selected base tray 12 does fit correctly or comfortably in the mouth of patient, meaning the base tray 12 is the correct size for the mouth of the patient, the method includes selecting the lip positioner insert 42.

The method further includes selecting one of the small upper lip positioner insert 64S, 66S, 68S, the medium upper lip positioner insert 64M, 66M, 68M, and the large upper lip positioner insert 64L, 66L, 68L of one of the right 64, center 66, and left 68 upper lip positioner inserts on the mouthpiece 10, coupling the selected upper lip positioner insert 44 to the upper portion 30 of the lip positioner support 18 on the selected base tray 12, positioning the selected base tray 12 with the selected upper lip positioner insert 44 in the mouth of the patient, and inspecting the fit of the upper lip positioner insert 44 on the assembled mouthpiece 10 in the mouth of the patient.

The inspecting step includes determining if the selected upper lip positioner insert 44 fits correctly or comfortably in the mouth of the patient. If the selected upper lip positioner insert 44 does not fit correctly or comfortably, meaning the upper lip positioner insert 44 does not separate the soft tissue of the upper lip and gums of the patient, the method includes selecting a different size upper lip positioner insert 44 and repeating the positioning and inspecting steps until the upper lip positioner insert 44 with the correct fit and comfort is selected for the patient. If the selected upper lip positioner insert 44 does fit correctly or comfortably in the mouth of patient, meaning the selected upper lip positioner insert 44 does separate the soft tissue of the upper lip and gums of the patient, the method includes repeating the selecting, positioning, and inspecting step for one of the other right side 64, forward center 66, left side 68 of the mouthpiece 10.

The method further includes selecting one of the small, medium, and large bottom lip positioner insert 46 of the desired location on the mouthpiece 10, coupling the selected bottom lip positioner insert 46 to the bottom portion 34 of the lip positioner support 18 on the selected base tray 12, positioning the selected base tray 12 with the selected bottom lip positioner insert 46 in the mouth of the patient, and inspecting the fit of the bottom lip positioner insert 46 on the mouthpiece 10 in the mouth of the patient.

The inspecting step includes determining if the selected bottom lip positioner insert 46 fits correctly or comfortably in the mouth of the patient. If the selected bottom lip positioner insert 46 does not fit correctly or comfortably, meaning the bottom lip positioner insert 46 does not separate the soft tissue of the bottom lip and gums of the patient, the method includes selecting a different size bottom lip positioner insert 46 and repeating the positioning and inspecting steps until the bottom lip positioner insert 46 with the correct fit and comfort is selected for the patient. If the selected bottom lip positioner insert 46 does fit correctly or comfortably in the mouth of patient, meaning the bottom lip positioner insert 46 does separate the soft tissue of the bottom lip and gums of the patient, the method includes repeating the selecting, positioning, and inspecting step for one of the other right side 70, forward center 72, and left side 74 of the mouthpiece 10.

In the illustrative embodiment, the method includes selecting one of the small lip positioner insert, the medium lip positioner insert, and the large lip positioner insert for each of the right, left, and forward center lip positioner inserts for both the upper and bottom lip positioner supports.

In other embodiments, the method includes selecting one of the small lip positioner insert, the medium lip positioner insert, and the large lip positioner insert for each of the upper lip positioner insert and the bottom lip positioner insert.

The method further includes determining the desired orientation of the tongue within the mouth of the patient, selecting one of the left tongue guide insert 36L, the center tongue guide insert 36C, and the right tongue insert 36R, and coupling the selected tongue guide insert 36 to the U-shaped bite tray 16 of the selected base tray 12 to form an assembled mouthpiece 10. The coupling step includes engaging the attachment tabs 54, 56, 58 of the selected tongue guide insert 36 with the corresponding attachment channels 22, 82, 84 formed in the bite plate 16 of the base tray 12.

The method further includes positioning the assembled modular mouthpiece 10 within the mouth of the patient so that the selected base tray 12 is arranged between upper and lower teeth of the patient, the selected tongue guide insert 36 is engaged with the tongue of the patient in the desired orientation within the mouth of the patient, and the selected lip positioner inserts 44, 46 are engaged with the gums and lips of the patient to separate the soft tissue of the gums and lips of the patient. The method further includes exposing the mouth of the patient to radiation.

The method may further include installing a suction device within the main suction channel 22 in the bite plate 16 of the base tray 12 and suctioning fluids out of the mouth of the patient through the main suction channel 22. The method may further include inspecting the indicator tab 23 to ensure the tongue of the patient is in the desired position.

Figure 8:
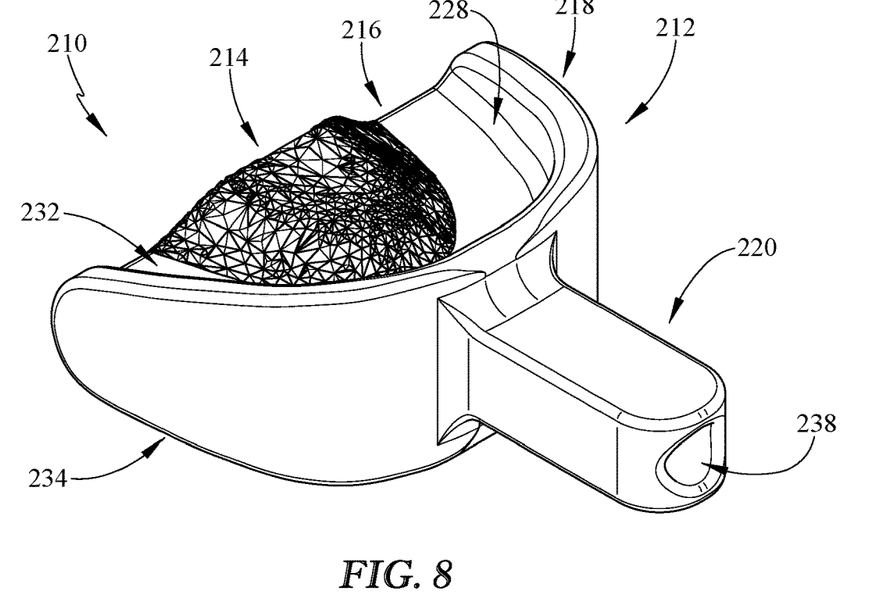
FIG. 8 is a perspective view of another embodiment of a mouthpiece for soft tissue location during oral therapies showing the mouthpiece is a single integral component.
Figure 9:
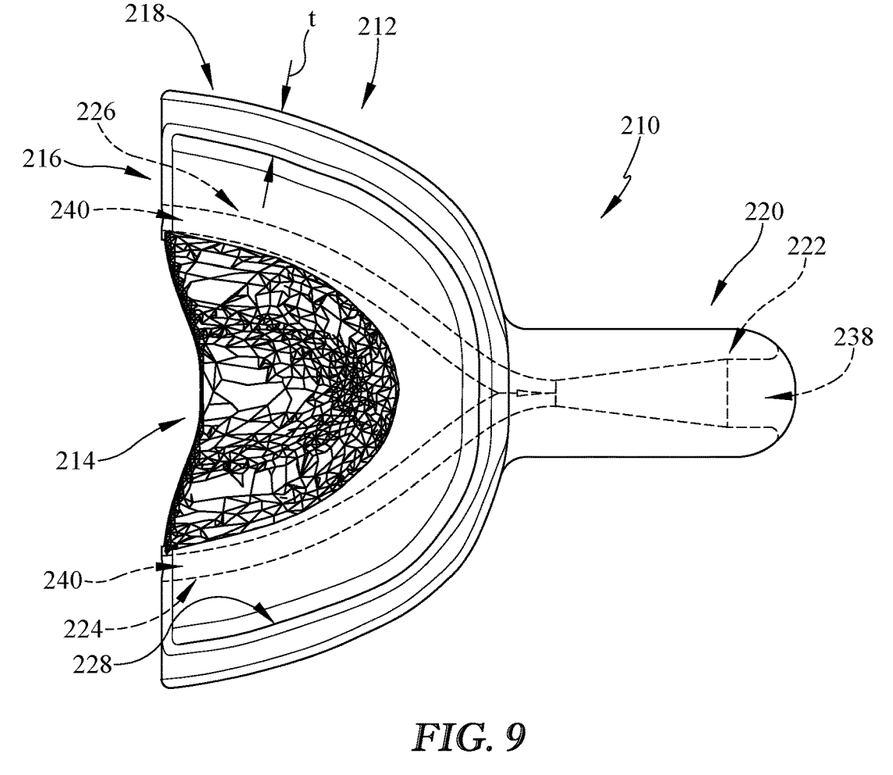
FIG. 9 is a top view of the mouthpiece of FIG. 8.

Another embodiment of a mouthpiece 210 in accordance with the present disclosure is shown in FIGS. 8 and 9. The mouthpiece 210 is substantially similar to the modular mouthpiece 10 shown in FIGS. 1-7 and described herein. Accordingly, similar reference numbers in the 200 series indicate features that are common between the modular mouthpiece 10 and the modular mouthpiece 210. The description of the modular mouthpiece 10 is incorporated by reference to apply to the modular mouthpiece 210, except in instances when it conflicts with the specific description and the drawings of the modular mouthpiece 210.

The mouthpiece 210 includes a base tray 212 and a tongue guide 214 as shown in FIGS. 8 and 9. The tongue guide 214 is integrally formed with the base tray 212 to form the mouthpiece 210. The mouthpiece 210 may be 3D printed so that the base tray 212 and tongue guide 214 may be customized to the mouth of the patient.

The base tray 212 includes a U-shaped bite plate 216, a lip positioner support 218, a handgrip 220 a as shown in FIGS. 8 and 9. The U-shaped bit plate 216 is configured to be arranged between upper and lower teeth of the patient. The lip positioner support 218 extends from an outer edge 228 of the U-shaped bite plate 216 and is configured to engage lips and gums of the patient to separate the soft tissue of the lips and gums of the patient.

The handgrip 220 extends from the lip positioner support 218 at a front center of the modular mouthpiece 210. The handgrip 220 is configured to provide a handle for positioning the mouthpiece 210 within the mouth of the patient.

The base tray 212 is also shaped to include a plurality of channels 222, 224, 226 as shown in FIG. 9. The plurality of channels 22, 24, 26 extend through the base tray 212 and are configured to provide breathing passageways for the patient. The channels 222, 224, 226 may also provide a passageway for suctioning fluids out of the mouth of the patient.

In the illustrative embodiment, the plurality of channels include a main channel 222 and auxiliary channels 224, 226 as shown in FIG. 9. The main channel 222 extends through the handgrip 220. The auxiliary channels 224, 226 extend through the bite plate 216 around the tongue guide 214. The main channel 222 converges with the auxiliary channels 224, 226 so that the main channel 222 is in fluid communication with the auxiliary channels 224, 226 to provide a fluid connection between an opening 238 of the channel 222 on the handgrip 220 and openings 240 of the auxiliary channels 224, 226.

The lip positioner support 218 includes an upper portion 232 and a bottom portion 234 as shown in FIG. 8. The upper portion 232 extends upwardly from the outer edge 228 of the bite plate 216 around the upper teeth of the patient, while the bottom portion 234 extends downwardly from the outer edge 228 of the bite plate 216 around the bottom teeth of the patient. The upper portion 232 is configured to engage an upper lip and gums of the patient. The bottom portion 234 is configured to engage a bottom lip and gums of the patient.

In the illustrative embodiment, the lip positioner support 218 has a thickness t as shown in FIG. 9. The thickness t of the lip positioner support 218 may vary along the outer edge 228 of the base tray 212 so that the lip positioner support 218 separates the lips and gums of the patient, while correctly and comfortably fitting in the mouth of the patient. The 3D printing of the mouthpiece 210 may allow the thickness t of the lip positioner support 218 to be customized to the mouth of the patient.

The tongue guide 214 may be customized to position the tongue toward one of a right side, center, and left side of the mouth of the patient. The 3D printing of the mouthpiece 210 may allow the tongue guide 214 to be sized correctly so as to fit the tongue of the patient within the tongue guide 214.

A method may include several steps. The method may include taking a mold of the mouth of the patient with the tongue, lips, and other soft tissues accurately positioned in a desired orientation within the mouth of the patient, 3D printing the mold to make a model of the patient specific mouthpiece 210, positioning the patient specific mouthpiece 210 within the mouth of the patient, and inspecting the fit of the mouthpiece 210 in the mouth of the patient.

The inspecting step includes determining if the mouthpiece 210 fits correctly or comfortably in the mouth of the patient. If the mouthpiece 210 does not fit correctly or comfortably in the mouth of the patient, the method includes repeating the molding and 3D printing steps until the mouthpiece 210 with the correct fit and comfort is created for the patient. If the mouthpiece 210 does fit correctly or comfortably in the mouth of patient, the method includes installing a suction device within the main channel 222 in the bite plate 216 of the base tray 212, suctioning fluids out of the mouth of the patient through the main channel 222, and exposing the mouth of the patient to radiation.

The present disclosure related to a modular mouthpiece 10 for soft tissue location during oral therapies, such as radiation for cancer treatment. The modular mouthpiece 10 may be configured to gently and accurately position the tongue of the patient to the left, right, or center of the mouth of the patient depending on which insert 36R, 36C, 36L is used. The modular mouthpiece 10 may also be configured to separate the lip tissue from the other tissue such as the gums of the patient to varying degrees depending on which inserts 64, 66, 68 are used. The modular mouthpiece 10 may also be configured to allow airflow through the mouthpiece 10 so that the patient may breathe easily.

The modular mouthpiece 10 may give patients access to a personalized medical product that may comfortably and accurately position the oral anatomy of the patient in such a way that may help the treatment or radiation beam reach the intended target and avoid the healthy tissue. The modular mouthpiece kit 90 may allow the patient to customize the modular mouthpiece 10, or an integral fully customized mouthpiece 210 may be made for difficult or non-standard cases.

The mouthpiece 10, 210 may be 3D printed. The mouthpiece 10, 210 may be 3D printed using biocompatible material.

The 3D printed mouthpiece 10, 210 may be configured to repeatedly and accurately positon the mandible and tongue throughout multi-session therapies, especially radiation therapy. Accurate, repeatable positioning of the mandible and tongue throughout the radiation treatment may allow for maximum possible dose of radiation to reach the intended target areas while bypassing healthy bone and tissue.

Current techniques involve the use of one or more foam bite blocks and do not provided accurate, repeatable positioning of the mandible and tongue of the patient. This may cause unintended areas to absorb the radiation. However, the mouthpiece 10, 210 may be configured to position the mandible and tongue, may have detachable side panels to push the lips out as needed, and may have a reversible or customizable tongue flange 50, 214 that gently guides the tongue to a desired orientation within the mouth.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

What is claimed is:

1. A modular mouthpiece for soft tissue location during oral therapies, the modular mouthpiece comprising
a base tray including a U-shaped bite plate configured to be arranged between upper and lower teeth of a patient and a lip positioner support that extends from an outer edge of the U-shaped bite plate, and
soft tissue placement inserts including (i) a tongue guide insert selectively coupled to the U-shaped bite plate of the base tray that is configured to engage a tongue of the patient to position the tongue in a desired orientation within the mouth of the patient and (ii) at least one lip positioner insert selectively coupled to the lip positioner support of the base tray that is configured to engage a lip and gums of the patient to separate the soft tissue of the lip and gums of the patient.

2. The modular mouthpiece of claim 1, wherein the lip positioner support includes an upper portion that extends upwardly from the outer edge of the U-shaped bite plate around the upper teeth of the patient and a bottom portion that extends downwardly from the outer edge of the U-shaped bite plate around the bottom teeth of the patient, and wherein the soft tissue placement inserts include at least one upper lip positioner insert selectively coupled to the upper portion of the lip positioner support and configured to engage an upper lip and gums of the patient and at least one bottom lip positioner inserter selectively coupled to the bottom portion of the lip positioner support and configured to engage a bottom lip and gums of the patient.

3. The modular mouthpiece of claim 2, wherein the soft tissue placement inserts includes a plurality of upper lip positioner inserts, the plurality of lip positioner inserts including a right upper positioner insert selectively coupled to the upper portion of the lip positioner support on a right side of the base tray, a center upper positioner insert selectively coupled to the upper portion of the lip positioner support on a front center of the base tray, and a left upper positioner insert selectively coupled to the upper portion of the lip positioner support on a left side of the base tray.

4. The modular mouthpiece of claim 3, wherein the tongue insert guide includes a tongue guide base configured to be selectively coupled to an inner edge of the U-shaped bite plate of the base tray.

5. The modular mouthpiece of claim 2, wherein the soft tissue placement inserts includes a plurality of bottom lip positioner inserts, the plurality of bottom lip positioner inserts including a right bottom positioner insert selectively coupled to the bottom portion of the lip positioner support on a right side of the base tray, a center bottom positioner insert selectively coupled to the bottom portion of the lip positioner support on a front center of the base tray, and a left bottom positioner insert selectively coupled to the bottom portion of the lip positioner support on a left side of the base tray.

6. The modular mouthpiece of claim 1, further comprising a position indicator tab coupled to the base tray and configured to move relative to the lip positioner support between a retracted position in which the position indicator tab is flush with the lip positioner support and an extended position in which the position indicator tab extends from the lip positioner support to indicate when the tongue of the patient is in the desired orientation relative to the tongue guide insert.

7. The modular mouthpiece of claim 6, wherein the modular mouthpiece includes two position indicator tabs with one position indicator tab located on one of the right side of the base tray and the other located on the left side of the base tray.

8. The modular mouthpiece of claim 6, wherein the position indicator tab includes a color at an end of the position indicator tab extending from lip positioner support.

9. The modular mouthpiece of claim 1, wherein the base tray further includes a handgrip that extends from the bite plate at a front center of the base tray and the hand grip is configured to provide a handle for positioning the modular mouthpiece in the desired orientation within the mouth of the patient.

10. The modular mouthpiece of claim 1, wherein the tongue insert guide includes a tongue guide base that underlies the tongue of the patient and configured to be selectively coupled to an inner edge of the U-shaped bite plate of the base tray and a tongue guide flange that extends upwardly from the tongue guide base and engages the tongue of the patient to position the tongue toward one of a right side of the mouth of the patient, a center of the mouth of the patient, and a left side of the mouth of the patient.

11. The modular mouthpiece of claim 1, wherein the U-shaped bite tray is shaped to include at least one passageway that extends through the U-shaped bite tray and the tongue guide insert is shaped to include a guide passageway that extends through the tongue guide insert to provide fluid communication from a free edge of the tongue guide insert to the at least one passageway of the U-shaped bite tray when the tongue guide insert is coupled to the U-shaped bite tray of the base tray so that the at least one passageway and the guide passageway provide a breathing passageway for the patient while the modular mouthpiece is located in a mouth of the patient.

12. A method comprising
providing one of a small base tray, a medium base tray, and a large base tray, each base tray including a U-shaped bite plate configured to be arranged between upper and lower teeth of a patient and a lip positioner support that extends from an outer edge of the U-shaped bite plate around the upper and lower teeth of the patient,
providing one of a left tongue guide insert configured to urge a tongue of the patient to a left side of the mouth of the patient, a center tongue insert configured to urge the tongue of the patient to a center of the mouth of the patient, and a right tongue guide insert configured to urge the tongue of the patient to a right side of the mouth of the patient,
providing a small lip positioner insert, a medium lip positioner insert, and a large lip positioner insert,
selecting one of the small base tray, the medium base tray, and the large base tray,
selecting one of the left tongue guide insert, the center tongue guide insert, and the right tongue insert,
coupling the selected tongue guide insert to the U-shaped bite tray of the selected base tray,
selecting one of the small lip positioner insert, the medium lip positioner insert, and the large lip positioner insert,
coupling the selected lip positioner insert to the lip positioner support on the selected base tray to provide an assembled modular mouthpiece,
positioning the assembled modular mouthpiece within the mouth of the patient so that the U-shaped bit tray is arranged between upper and lower teeth of the patient, the selected tongue guide insert is engaged with the tongue of the patient in the desired orientation within the mouth of the patient, and the selected lip positioner insert is engaged with the gums and lip of the patient to separate the soft tissue of the gums and lips of the patient, and
exposing the mouth of the patient to radiation.

13. The method of claim 12 further comprising providing a small upper lip positioner insert, a medium upper lip positioner insert, and a large upper lip positioner insert, selecting one of the small upper lip positioner insert, the medium upper lip positioner insert, and the large upper lip positioner insert, coupling the selected upper lip positioner insert to an upper lip positioner support of the base tray.

14. The method of claim 12 further comprising providing a small bottom lip positioner insert, a medium bottom lip positioner insert, and a large bottom lip positioner insert, selecting one of the small bottom lip positioner insert, the medium bottom lip positioner insert, and the large bottom lip positioner insert, and coupling the selected bottom lip positioner insert to a bottom lip positioner support of the base tray.

15. The method of claim 12 further comprising suctioning fluids out of the mouth of the patient through a suction channel formed to extend through the U-shaped bite tray.

16. A modular mouthpiece kit for soft tissue location during oral therapies, the modular mouthpiece kit comprising
a plurality of base trays including a small base tray, a medium base tray, and a large base tray, each base tray of the plurality of base trays including a U-shaped bite plate configured to be arranged between upper and lower teeth of a patient and a lip positioner support that extends from an outer edge of the U-shaped bite plate around the upper and lower teeth of the patient,
a plurality of tongue guide inserts configured to be selectively coupled to the U-shaped bite plate of each base tray, the plurality of tongue guide inserts including a left tongue guide insert configured to urge a tongue of the patient to a left side of the mouth of the patient, a center tongue insert configured to urge the tongue of the patient to a center of the mouth of the patient, and a right tongue guide insert configured to urge the tongue of the patient to a right side of the mouth of the patient, and a plurality of lip positioner inserts configured to be selectively coupled to the lip positioner support of each base tray, the plurality of lip positioner inserts including a plurality of upper lip positioner inserts configured to engage an upper lip and gums of the patient to separate the soft tissue of the upper lip and gums of the patient and a plurality of bottom lip positioner inserts configured to engage a bottom lip and gums of the patient to separate the soft tissue of the bottom lip and gums of the patient, each of the plurality of upper and bottom lip positioner inserts including a small lip positioner insert, a medium positioner insert, and a larger positioner insert.

17. The modular mouthpiece kit of claim 16, wherein the small lip positioner insert has a first thickness, the medium lip positioner insert has a second thickness greater than the first thickness, and the large lip positioner insert has a third thickness greater than the second thickness.

18. The modular mouthpiece kit of claim 16, wherein the plurality of upper lip positioner inserts includes a plurality of right upper positioner inserts configured to be selectively coupled to the upper portion of the lip positioner support on a right side of the base tray, a plurality of center upper positioner inserts configured to be selectively coupled to the upper portion of the lip positioner support on a front center of the base tray, and a plurality of left upper positioner inserts selectively configured to be coupled to the upper portion of the lip positioner support on a left side of the base tray.

19. The modular mouthpiece of claim 16, wherein the plurality of bottom lip positioner inserts includes a plurality of right bottom positioner inserts selectively coupled to the bottom portion of the lip positioner support on a right side of the base tray, a plurality of center bottom positioner inserts selectively coupled to the bottom portion of the lip positioner support on a front center of the base tray, and a plurality of left bottom positioner inserts selectively coupled to the bottom portion of the lip positioner support on a left side of the base tray.

20. The modular mouthpiece kit of claim 16, further comprising a position indicator tab configured to be coupled to each plurality of base trays and configured to move relative to the lip positioner support between a retracted position in which the position indicator tab is flush with the lip positioner support and an extended position in which the position indicator tab extends from the lip positioner support to indicate when the tongue of the patient is in the desired orientation relative to the tongue guide insert.

* * * * *